(12) United States Patent
Abbitt et al.

(10) Patent No.: US 7,081,566 B2
(45) Date of Patent: Jul. 25, 2006

(54) SEED PREFERRED REGULATORY ELEMENTS

(75) Inventors: Shane E. Abbitt, Ankeny, IA (US); Rudolf Jung, Des Moines, IA (US); Jennifer A. Klaiber, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 211 days.

(21) Appl. No.: 10/414,588

(22) Filed: Apr. 16, 2003

(65) Prior Publication Data

US 2004/0210043 A1 Oct. 21, 2004

(51) Int. Cl.
*A01H 5/00* (2006.01)
*A01H 5/10* (2006.01)
*C12N 15/82* (2006.01)

(52) U.S. Cl. ................... 800/287; 435/320.1; 435/468; 536/24.1; 800/298

(58) Field of Classification Search ............... 536/24.1; 800/278, 287, 298; 435/320.1, 468, 419
See application file for complete search history.

(56) References Cited

U.S. PATENT DOCUMENTS 6,410,828 B1 * 6/2002 Armstrong et al. ......... 800/287

OTHER PUBLICATIONS

Fiedler et al 1993, Plant Molecular Biology 2:669-679.*
Donald et al 1990, The EMBO Journal 9(6):1717-1726.*

* cited by examiner

*Primary Examiner*—David H Kruse
(74) *Attorney, Agent, or Firm*—Pioneer Hi-Bred International, Inc.; Kathryn K. Lappegard

(57) ABSTRACT

The present invention provides compositions and methods for regulating expression of isolated nucleotide sequences in a plant. The compositions are novel nucleic acid sequences for seed-preferred regulatory sequences. Methods for expressing an isolated nucleotide sequence in a plant using the regulatory sequences are also provided. The methods comprise transforming a plant cell to contain an isolated nucleotide sequence operably linked to the seed-preferred regulatory sequences of the present invention and regenerating a stably transformed plant from the transformed plant cell.

10 Claims, No Drawings

SEED PREFERRED REGULATORY ELEMENTS

FIELD OF THE INVENTION

The present invention relates to the field of plant molecular biology, more particularly to regulation of gene expression in plants.

BACKGROUND OF THE INVENTION

Expression of isolated DNA sequences in a plant host is dependent upon the presence of operably linked regulatory elements that are functional within the plant host. Choice of the regulatory sequences will determine when and where within the organism the isolated DNA sequence is expressed. Where continuous expression is desired in all cells of a plant throughout development, constitutive promoters are utilized. In contrast, where gene expression in response to a stimulus is desired, inducible promoters are the regulatory element of choice. Where expression in particular tissues or organs are desired, sometimes at specific stages of development, tissue-preferred promoters and/or terminators are used. That is, these regulatory elements can drive expression in specific tissues or organs, at specific stages. Additional regulatory sequences upstream and/or downstream from the core sequences can be included in expression cassettes of transformation vectors to bring about varying levels of expression of isolated nucleotide sequences in a transgenic plant.

Seed development involves embryogenesis and maturation events as well as physiological adaptation processes that occur within the seed to insure progeny survival. Developing plant seeds accumulate and store carbohydrate, lipid, and protein that are subsequently used during germination. Generally, the expression patterns of seed proteins are highly regulated. This regulation includes spatial and temporal regulation during seed development. A variety of proteins accumulate and decay during embryogenesis and seed development and provide an excellent system for investigating different aspects of gene regulation as well as for providing regulatory sequences for use in genetic manipulation of plants.

As the field of plant bioengineering develops, and more genes become accessible, a greater need exists for transforming with multiple genes. These multiple exogenous genes typically need to be controlled by separate regulatory sequences. Some genes should be regulated constitutively whereas other genes should be expressed at certain developmental stages or location in the transgenic organism. Accordingly, a variety of regulatory sequences having diverse effects is needed.

Another reason why diverse regulatory sequences are needed is that undesirable biochemical interactions result from using the same regulatory sequence to control more than one gene. For example, transformation with multiple copies of a regulatory element may cause homologous recombination between two or more expression systems, formation of hairpin loops caused from two copies of the same promoter or enhancer in opposite orientation in close proximity, competition between identical expression systems for binding to common promoter-specific regulatory factors, and inappropriate expression levels of an exogenous gene due to trans effects of a second promoter or enhancer.

In view of these considerations, a goal in this field has been the detection and characterization of new regulatory sequences for transgenic control of DNA constructs.

Isolation and characterization of seed-preferred promoters and terminators that can serve as regulatory elements for expression of isolated nucleotide sequences of interest in a seed-preferred manner are needed for improving seed traits in plants.

DETAILED DESCRIPTION OF THE INVENTION

In accordance with the invention, nucleotide sequences are provided that allow initiation of transcription in seed. The sequences of the invention comprise transcriptional initiation regions associated with seed formation and seed tissues. Thus, the compositions of the present invention comprise novel nucleotide sequences for plant regulatory elements natively associated with the nucleotide sequences coding for maize EAP1.

A method for expressing an isolated nucleotide sequence in a plant using the transcriptional initiation sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a seed-preferred manner.

Under the transcriptional regulation of the seed-specific regulatory elements will be a sequence of interest which will provide for modification of the phenotype of the seed. Such modification includes modulating the production of an endogenous product, as to amount, relative distribution, or the like, or production of an exogenous expression product to provide for a novel function or product in the seed.

By "seed-preferred" is intended favored spatial expression in the seed, including at least one of embryo, kernel, pericarp, endosperm, nucellus, aleurone, pedicel, and the like.

By "embryo-preferred" is intended favored spatial expression in the embryo of the seed.

By "regulatory element" is intended sequences responsible for tissue and temporal expression of the associated coding sequence including promoters, terminators, enhancers, introns, and the like.

By "terminator" is intended sequences that are needed for termination of transcription: a regulatory region of DNA that causes RNA polymerase to disassociate from DNA, causing termination of transcription.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression.

By "natively associated with" is intended that which normally accompanies or interacts with material as found in its naturally occurring environment.

The term "monocot" means the group of flowering plants having a single cotyledon.

The term "dicot" means the group of flowering plants having two cotyledons (seed leaves).

By "regulates" or "regulates transcription" means controlling expression by means of controlling transcription.

The maize EAP1 (Early Abundant Protein 1) coding region is represented by SEQ ID NOS: 7 and 8. This coding region is a distant phaseolin-like homologue of globulin 1, a fragment of which is labeled "antimicrobial peptide" in the public databases. This gene name was based on a fragment (33 amino acids) of the gene product that was found to have antimicrobial activity in corn grain (described in U.S. Pat. No. 5,905,187) and was not based on conserved or functional motifs. It is expressed in maize embryo as early as 12 days after pollination (dap) but most strongly from 18–35 dap; hence the designation "Embryo Abundant Protein 1".

The isolated promoter sequences of the present invention can be modified to provide for a range of expression levels of the isolated nucleotide sequence. Less than the entire promoter region can be utilized and the ability to drive seed-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts.

Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' untranslated regions flanking its respective transcription initiation site. Likewise the terminator can be isolated from the 3' untranslated region flanking its respective stop codon.

The term "isolated" refers to material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of regulatory elements are well known in the art. One method is the use of primers and genomic DNA used in conjunction with the GenomeWalker Kit™ (Clontech). The sequences for the regulatory elements are set forth in SEQ ID NOS: 1 and 2.

The Eap1 promoter set forth in SEQ ID NO: 1 is 1268 nt in length with putative TATA motifs located at positions 707–712 and 1126–1130; and putative CAAT motifs at positions 659–661 and 1091–1093. The promoter can be isolated with the primers of SEQ ID NOS: 3 and 4. It expresses as early as 12 days after pollination (dap) but most strongly expresses at 18–35 dap. The EAP1 promoter can address expression problems by providing expression primarily in the embryo with some expression in developing aleurone from mid through late development.

The Eap1 terminator set forth in SEQ ID NO: 2 is 762 nucleotides in length. The terminator was isolated from a coding sequence found in maize tissue libraries of 12 to 20 DAP (days after pollination) embryo. The terminator can be isolated with the primers/probes of SEQ ID NOS: 5 and 6. The Eap1 terminator, with the appropriate promoter, can provide expression during early embryo development. The Eap1 terminator can be used with the Eap1 promoter in an expression cassette, or can be used with another appropriate promoter to provide seed-preferred expression of a coding region.

The regulatory elements of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably, plants include corn, soybean, sunflower, safflower, canola, wheat, barley, rye, alfalfa, and sorghum.

Regulatory sequences from other plants may be isolated according to well-known techniques based on their sequence homology to the regulatory sequences set forth herein. In these techniques, all or part of the known regulatory sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire regulatory sequence or portions thereof can be used as a probe capable of specifically hybridizing to corresponding regulatory sequences. To achieve specific hybridization under a variety of conditions, such probes include sequences that are unique and are preferably at least about 10 nucleotides in length, and most preferably at least about 20 nucleotides in length. Such probes can be used to amplify corresponding regulatory sequences from a chosen organism by the well-known process of polymerase chain reaction (PCR). This technique can be used to isolate additional regulatory sequences from a desired organism or as a diagnostic assay to determine the presence of the regulatory sequence in an organism. Examples include hybridization screening of plated DNA libraries (either plaques or colonies; see e.g. Innis et al. (1990) PCR Protocols, A Guide to Methods and Applications, eds., Academic Press).

The terms "stringent conditions" or "stringent hybridization conditions" includes reference to conditions under which a probe will hybridize to its target sequence, to a detectably greater degree than other sequences (e.g., at least 2-fold over background). Stringent conditions are target-sequence dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 250 nucleotides in length to about 1000 nucleotides in length.

An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995). See also Sambrook et al. (1989) Molecular Cloning: A Laboratory Manual (2nd ed. Cold Spring Harbor Laboratory, Cold Spring Harbor, N.Y.).

In general, sequences that correspond to the regulatory sequences of the present invention and hybridize to the regulatory sequence disclosed herein will be at least 50% homologous, 55% homologous, 60% homologous, 65% homologous homologous, 95% homologous and even 98% homologous or more with the disclosed sequence.

Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

Hybridization conditions for the regulatory sequences of the invention include hybridization at 42° C. in 50% (w/v) formamide, 6×SSC, 0.5% (w/v) SDS, 100 µg/ml salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating. Exemplary high stringency conditions include a wash in 2×SSC, 0.5% (w/v) SDS, at 65° C. for 30 minutes and repeating. Sequences that correspond to the regulatory sequences of the present invention may be obtained using all the above conditions.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters.

Methods of aligning sequences for comparison are well known in the art. Gene comparisons can be determined by conducting BLAST (Basic Local Alignment Search Tool; Altschul, S. F., et al., (1993) J. Mol. Biol. 215:403–410) searches under default parameters for identity to sequences contained in the BLAST "GENEMBL" database. A sequence can be analyzed for identity to all publicly available DNA sequences contained in the GENEMBL database using the BLASTN algorithm under the default parameters. Identity to the sequence of the present invention would mean a polynucleotide sequence having at least 65% sequence identity, more preferably at least 70% sequence identity, more preferably at least 75% sequence identity, more preferably at least 80% identity, more preferably at least 85% sequence identity, more preferably at least 90% sequence identity and most preferably at least 95% sequence identity wherein the percent sequence identity is based on the entire promoter region.

GAP uses the algorithm of Needleman and Wunsch (J. Mol. Biol. 48:443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89:10915).

Sequence fragments of the present invention refer to those fragments of a particular regulatory element disclosed herein that operate to promote expression in the seed embryo of an operably linked isolated nucleotide sequence from 18 to 35 days after pollination (DAP). These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis et al. (1987) Methods Enzymol. 155:335–350, and Erlich, ed. (1989) PCR Technology (Stockton Press, New York). Again, variants of these fragments, such as those resulting from site-directed mutagenesis, are encompassed by the compositions of the present invention.

Nucleotide sequences comprising at least about 20 contiguous sequences of the sequence set forth in SEQ ID NOS: 1 are encompassed. These sequences can be isolated by hybridization, PCR, and the like. Such sequences encompass fragments capable of driving seed-preferred expression, fragments useful as probes to identify similar sequences, as well as elements responsible for temporal or tissue specificity.

Biologically active variants of the regulatory sequences are also encompassed by the compositions of the present invention. A regulatory "variant" is a modified form of a regulatory sequence wherein one or more bases have been modified, removed or added and functionality of the element is retained. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

One example of a regulatory sequence variant is a promoter formed by one or more deletions from a larger promoter. The 5' portion of a promoter up to the TATA box near the transcription start site can be deleted without abolishing promoter activity, as described by Zhu et al., The Plant Cell 7:1681–89 (1995). Such variants should retain promoter activity, particularly the ability to drive expression in seed or seed tissues. Biologically active variants include, for example, the native regulatory sequences of the invention having one or more nucleotide substitutions, deletions or insertions. Activity can be measured by Northern blot analysis, reporter activity measurements when using transcriptional fusions, and the like. See, for example, Sambrook et al. (1989) Molecular Cloning: A Laboratory Manual (2nd ed. Cold Spring Harbor Laboratory, Cold Spring Harbor, N.Y.), herein incorporated by reference.

The nucleotide sequences for the seed-preferred regulatory elements disclosed in the present invention, as well as variants and fragments thereof, are useful in the genetic manipulation of any plant when operably linked with an isolated nucleotide sequence whose expression is to be controlled to achieve a desired phenotypic response. By "operably linked" is intended the transcription or translation of the isolated nucleotide sequence is under the influence of the regulatory sequence.

The nucleotide sequences for the regulatory elements of the invention can be provided in expression cassettes along with isolated nucleotide sequences for expression, known as a plant transcription unit. In a plant transcription unit, a first nucleotide sequence, generally the coding region of interest, is operably linked to at least a second and/or third nucleotide sequence that function as regulatory elements. These regulatory elements are minimally the promoter at the 5' end of the transcription unit, and the terminator at the 3' end. (see Genes IV, page 288, FIG. 11.2). There can in addition, be inserted other elements such as introns, enhancers, transit peptides and the like operably linked at locations within the transcription unit which have been shown to regulate the expression of the coding region in the desired manner.

In this manner, the nucleotide sequences for the regulatory elements of the invention may be provided in expression cassettes along with isolated nucleotide sequences for expression in the plant of interest, more particularly in the seed of the plant. Such an expression cassette is provided with a plurality of restriction sites for insertion of the nucleotide sequence to be under the transcriptional control of the regulatory elements.

The nucleotide sequence operably linked to the regulatory elements disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response.

Thus the regulatory sequences disclosed herein can be operably linked to antisense DNA sequences to reduce or inhibit expression of a native protein in the plant seed.

The expression cassette will also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

The Eap1 terminator can be used with the Eap1 promoter in an expression cassette, or can be used with another appropriate promoter to provide seed-preferred expression of a coding region.

Other convenient termination regions are available from the Ti-plasmid of A. tumefaciens, such as the octopine synthase and nopaline synthase termination regions. See also: Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. 1989) Nucleic Acids Res. 17:7891–7903; Joshi et al. (1987) Nucleic Acid Res. 15:9627–9639.

The expression cassettes can additionally contain 5' leader sequences. Such leader sequences can act to enhance translation. Translation leaders are known in the art and include: picornavirus leaders, for example: EMCV leader (Encephalomyocarditis 5' noncoding region), Elroy-Stein et al. (1989) Proc. Nat. Acad. Sci. USA 86:6126–6130; potyvirus leaders, for example, TEV leader (Tobacco Etch Virus), Allison et al. (1986); MDMV leader (Maize Dwarf Mosaic Virus), Virology 154:9–20; human immunoglobulin heavy-chain binding protein (BiP), Macejak et al. (1991) Nature 353:90–94; untranslated leader from the coat protein mRNA of alfalfa mosaic virus (AMV RNA 4), Jobling et al. (1987) Nature 325:622–625); tobacco mosaic virus leader (TMV), Gallie et al. (1989) Molecular Biology of RNA, pages 237–256; and maize chlorotic mottle virus leader (MCMV) Lommel et al. (1991) Virology 81:382–385. See also Della-Cioppa et al. (1987) Plant Physiology 84:965–968. The cassette can also contain sequences that enhance translation and/or mRNA stability such as introns.

In those instances where it is desirable to have the expressed product of the isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

The genes of interest expressed by the regulatory elements of the invention can be used for varying the phenotype of seeds. This can be achieved by increasing expression of endogenous or exogenous products in seeds. Alternatively, the results can be achieved by providing for a reduction of expression of one or more endogenous products, particularly enzymes or cofactors in the seed. These modifications result in a change in phenotype of the transformed seed. It is recognized that the regulatory elements may be used with their native coding sequences to increase or decrease expression resulting in a change in phenotype in the transformed seed.

General categories of genes of interest for the purposes of the present invention include for example, those genes involved in information, such as Zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms. It is recognized that any gene of interest, including the native coding sequence, can be operably linked to the regulatory elements of the invention and expressed in the seed.

Modifications that affect grain traits include increasing the content of oleic acid, or altering levels of saturated and unsaturated fatty acids. Likewise, increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997; the disclosures of which are incorporated herein by reference. Another example is lysine and/or sulfur-rich seed protein encoded by the soybean 2S albumin described in WO 9735023 filed Mar. 20, 1996, and the chymotrypsin inhibitor from barley, Williamson et al. (1987) Eur. J. Biochem. 165:99–106, the disclosures of each are incorporated by reference.

Derivatives of the following genes can be made by site-directed mutagenesis to increase the level of preselected amino acids in the encoded polypeptide. For example, the gene encoding the barley high lysine polypeptide (BHL), is derived from barley chymotrypsin inhibitor, WO 9820133 filed Nov. 1, 1996 the disclosure of which is incorporated herein by reference. Other proteins include methionine-rich plant proteins such as from sunflower seed, Lilley et al. (1989) Proceedings of the World Congress on Vegetable Protein Utilization in Human Foods and Animal Feedstuffs; Applewhite, H. (ed.); American Oil Chemists Soc., Champaign, Ill. 497–502, incorporated herein by reference; corn, Pedersen et al. (1986) J. Biol. Chem. 261:6279; Kirihara et al. (1988) Gene 71:359, both incorporated herein by reference; and rice, Musumura et al. (1989) Plant Mol. Biol. 12:123, incorporated herein by reference. Other important genes encode glucans, Floury 2, growth factors, seed storage factors and transcription factors.

Agronomic traits in seeds can be improved by altering expression of genes that: affect the response of seed growth and development during environmental stress, Cheikh-N et al. (1994) Plant Physiol. 106(1):45–51) and genes controlling carbohydrate metabolism to reduce kernel abortion in maize, Zinselmeier et al. (1995) Plant Physiol. 107(2): 385–391.

Insect resistance genes may encode resistance to pests that have great yield drag such as rootworm, cutworm, European Corn Borer, and the like. Such genes include, for example: *Bacillus thuringiensis* endotoxin genes, U.S. Pat. Nos. 5,366,892; 5,747,450; 5,737,514; 5,723,756; 5,593,881; Geiser et al. (1986) Gene 48:109; lectins, Van Damme et al. (1994) Plant Mol. Biol. 24:825; and the like.

Genes encoding disease resistance traits include: detoxification genes, such as against fumonosin (WO 9606175 filed Jun. 7, 1995); avirulence (avr) and disease resistance (R) genes, Jones et al. (1994) Science 266:789; Martin et al. (1993) Science 262:1432; Mindrinos et al. (1994) Cell 78:1089; and the like.

Commercial traits can also be encoded on a gene(s) which could alter or increase for example, starch for the production of paper, textiles and ethanol, or provide expression of proteins with other commercial uses.

Exogenous products include plant enzymes and products as well as those from other sources including prokaryotes and other eukaryotes. Such products include enzymes, cofactors, hormones, and the like. The level of seed proteins, particularly modified seed proteins having improved amino acid distribution to improve the nutrient value of the seed can be increased. This is achieved by the expression of such proteins having enhanced amino acid content.

As noted herein, the present invention provides vectors capable of expressing genes of interest under the control of the regulatory elements. In general, the vectors should be functional in plant cells. At times, it may be preferable to have vectors that are functional in E. coli (e.g., production of protein for raising antibodies, DNA sequence analysis, construction of inserts, obtaining quantities of nucleic acids). Vectors and procedures for cloning and expression in E. coli are discussed in Sambrook et al. (supra).

The transformation vector comprising the regulatory sequences of the present invention operably linked to an isolated nucleotide sequence in an expression cassette, can also contain at least one additional nucleotide sequence for a gene to be co-transformed into the organism. Alternatively, the additional sequence(s) can be provided on another transformation vector.

Vectors that are functional in plants can be binary plasmids derived from Agrobacterium. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in E. coli can be used.

Reporter genes can be included in the transformation vectors. Examples of suitable reporter genes known in the art can be found in, for example: Jefferson et al. (1991) in Plant Molecular Biology Manual, ed. Gelvin et al. (Kluwer Academic Publishers), pp. 1–33; DeWet et al. (1987) Mol. Cell. Biol. 7:725–737; Goff et al. (1990) EMBO J. 9:2517–2522; Kain et al. (1995) BioTechniques 19:650–655; and Chiu et al. (1996) Current Biology 6:325–330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella et al. (1983) EMBO J. 2:987–992; methotrexate, Herrera Estrella et al. (1983) Nature 303:209–213; Meijer et al. (1991) Plant Mol. Biol. 16:807–820; hygromycin, Waldron et al. (1985) Plant Mol. Biol. 5:103–108; Zhijian et al. (1995) Plant Science 108:219–227; streptomycin, Jones et al. (1987) Mol. Gen. Genet. 210:86–91; spectinomycin, Bretagne-Sagnard et al. (1996) Transgenic Res. 5:131–137; bleomycin, Hille et al. (1990) Plant Mol. Biol. 7:171–176; sulfonamide, Guerineau et al. (1990) Plant Mol. Biol. 15:127–136; bromoxynil, Stalker et al. (1988) Science 242:419–423; glyphosate, Shaw et al. (1986) Science 233:478–481; phosphinothricin, DeBlock et al. (1987) EMBO J. 6:2513–2518.

Other genes that could serve utility in the recovery of transgenic events but might not be required in the final product would include, but are not limited to: GUS (β-glucoronidase), Jefferson (1987) Plant Mol. Biol. Rep. 5:387); GFP (green florescence protein), Chalfie et al. (1994) Science 263:802; luciferase, Teeri et al. (1989) EMBO J. 8:343; and the maize genes encoding for anthocyanin production, Ludwig et al. (1990) Science 247:449.

The transformation vector comprising the particular regulatory sequences of the present invention, operably linked to an isolated nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) Biotechniques 4:320–334; electroporation, Riggs et al. (1986) Proc. Natl. Acad. Sci. USA 83:5602–5606; Agrobacterium-mediated transformation, see for example, Townsend et al. U.S. Pat. No. 5,563,055; direct gene transfer, Paszkowski et al. (1984) EMBO J. 3:2717–2722; and ballistic particle acceleration, see for example, Sanford et al. U.S. Pat. No. 4,945,050; Tomes et al. (1995) in Plant Cell, Tissue, and Organ Culture: Fundamental Methods, ed. Gamborg and Phillips (Springer-Verlag, Berlin); and McCabe et al. (1988) *Biotechnology* 6:923–926. Also see Weissinger et al. (1988) Annual Rev. Genet. 22:421–477; Sanford et al. (1987) Particulate Science and Technology 5:27–37 (onion); Christou et al. (1988) Plant Physiol. 87:671–674 (soybean); McCabe et al. (1988) Bio/Technology 6:923–926 (soybean); Datta et al. (1990) *Bio-technology* 8:736–740 (rice); Klein et al. (1988) Proc. Natl. Acad. Sci. USA 85:4305–4309 (maize); Klein et al. (1988) Biotechnology 6:559–563 (maize); Klein et al. (1988) Plant Physiol. 91:440–444 (maize); Fromm et al. (1990) Biotechnology 8:833–839; Hooydaas-Van Slogteren et al. (1984) Nature (London) 311:763–764; Bytebier et al. (1987) Proc. Natl. Acad. Sci. USA 84:5345–5349 (Liliaceae); De Wet et al. (1985) in The Experimental Manipulation of Ovule Tissues, ed. G. P. Chapman et al. (Longman, New York), pp.197–209 (pollen); Kaeppler et al. (1990) Plant Cell Reports 9:415–418; and Kaeppler et al. (1992) Theor. Appl. Genet. 84:560–566 (whisker-mediated transformation); D. Halluin et al. (1992) Plant Cell 4:1495–1505 (electroporation); Li et al. (1993) Plant Cell Reports 12:250–255 and Christou et al. (1995) Annals of Botany 75:407–413 (rice); Osjoda et al. (1996) Nature Biotechnology 14:745–750 (maize via Agrobacterium tumefaciens); all of which are herein incorporated by reference.

The cells that have been transformed can be grown into plants in accordance with conventional ways. See, for example, McCormick et al. (1986) Plant Cell Reports 5:81–84. These plants can then be grown and pollinated with the same transformed strain or different strains. The resulting hybrid having seed-preferred expression of the desired phenotypic characteristic can then be identified. Two or more generations can be grown to ensure that seed-preferred expression of the desired phenotypic characteristic is stably maintained and inherited.

The following examples are offered by way of illustration and not by way of limitation.

EXAMPLES

Example 1

Isolation of Positive Clones Using BAC (Bacterial Artificial Chromosome) Libraries The BAC library subjected to the screening procedure was produced from the maize Mo17 genotype using the protocol of Gubler and Hoffman (Gubler, U. et al. Gene, 1983; 25:263–269). Half of the library was created by partial digestions with HindIII and half with EcoRI. Both the Hind III and EcoRI portions of the library that were screened for the Eap1 probe consisted of approximately 167,000 clones. These clones were plated out on 22×22 cm2 agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C. Once sufficient colonies were picked, they were pinned onto 22×22 cm2 nylon membranes using Q-bot. Each membrane contained 36,864 colonies or 36,864 colonies. These membranes were placed onto agar plate with appropriate antibiotic. The plates were incubated at 37° C. for 21 hours.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 1 hour. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2nd Edition). The probe was used in colony hybridization. The 1.2 kb probe was created in a PCR reaction using the Qiagen Hotstart PCR kit (Cat #203203, Qiagen, Valencia, Calif.). Genomic DNA from maize line V3-4 A63 was amplified with a forward and reverse primer: SEQ ID NOS: 9 and 10. The PCR reaction was performed in a Bio-Rad icycler (Hercules, Calif.) thermal cycler. The following cycle parameters were used: 95° C. for 15 minutes, followed by 30 cycles of 94° C. for 40 seconds, 63° C. for 60 seconds, and 72° C. for 1 minute. Finally, the samples were held at 72° C. for 10 minutes and then at 4° C. until further analysis.

Once positive BACs were identified, a southern analysis using a HindIII digestion was performed on them to identify bands containing Eap1 for subcloning. The same probe was used to identify a fragment (~7 kb) which was positive for Eap1. BAC DNA was then digested with Hind III. The entire collection of fragments produced from the digestion were subcloned into the PBSIIKS+ cloning vector. The transformants were then plated on Q trays for colony hybridization. Colonies were then lifted to a membrane for hybridization to the EAP1 probe. Hybridization was carried out at 55° C. in 6×SSC/0.5% SDS, followed by a wash in 2×SSC/0.1% SDS.

Those colonies identified as positive for the EAP1 probe were grown up for DNA isolation. After the DNA isolation, a dot blot was performed to verify presence of the EAP1 probe in the subclone. The C3 HindIII subclone of BAC ID#003117 was positive for the EAP1 probe. Through sequencing of that subclone, sequence was obtained so that the primers could be designed for the isolation of the promoter and terminator regions.

Example 2

Isolation of Regulatory Sequences

For isolation of the Eap1 promoter region, two nonoverlapping gene-specific primers (37 and 44 bp in length) were designed from the sequence obtained from the BAC subclone that tested positive for the EAP1 probe (see Example 1). The primers were designed to amplify the region upstream of the coding sequence, i.e. the 5' untranslated region and promoter of EAP1. The PCR was performed with DNA from MO17 BAC ID#003117 as the template with the primers shown in SEQ ID NOS: 3 and 4, using the Qiagen Hotstar PCR kit (Cat# 203203, Valencia, Calif.).

For isolation of the Eap1 terminator region, two nonoverlapping gene-specific primers (26 and 50 bp in length) were designed from the sequence obtained from the BAC subclone that tested positive for the EAP1 probe (see Example 1). The primers were designed to amplify the region downstream of the coding sequence, i.e. the 3' untranslated region of EAP1. The PCR was performed with DNA from MO17 BAC ID#003117 as the template, with the primers shown in SEQ ID NOS: 5 and 6, using the Qiagen Hotstar PCR kit (Cat# 203203, Valencia, Calif.).

PCR was performed in a Bio-Rad icycler (Hercules, Calif.) thermal cycler using reagents supplied with the Quiagen HotstarTaq Kit (Quigen Cat#203205). The following cycle parameters were used: 1 cycle of 95° C. for 15 minutes, followed by 30 cycles of 94° C. for 40 seconds, 58° C. for 1 minute, and 72° C. for 1.5 minutes. Finally, the samples were held at 72° C. for 10 minutes and then at 4° C. until further analysis.

Example 3

Vector Construction

Promoter::GUS::terminator fusion constructs were prepared by the methods described below. All vectors were constructed using standard molecular biology techniques (Sambrook et al., Supra). A reporter gene and a selectable marker gene for gene expression and selection was inserted between the multiple cloning sites of the pBluescript cloning vector (Stratagene Inc.,11011 N. Torrey Pines Rd., La Jolla, Calif.; www.strategene.com). The ampicillin resistance gene was replaced with a kanamycin resistance gene to allow use in bombardment experiments. The reporter gene was the β-glucuronidase (GUS) gene (Jefferson, R. A. et al., 1986, Proc. Natl. Acad. Sci. (USA) 83:8447–8451) into whose coding region was inserted the second intron from the potato ST-LS1 gene (Vancanneyt et al., Mol. Gen. Genet. 220: 245–250, 1990), to produce GUSINT, in order to prevent expression of the gene in Agrobacterium (see Ohta, S. et al., 1990, Plant Cell Physiol. 31(6):805–813. The EAP1 promoter and terminator were ligated together to create an empty expression cassette. The GUSINT coding region was then cloned downstream of the EAP promoter but upstream of the EAP1 terminator to create the GUS expression cassette. The GUSINT coding region was ligated in frame to the NcoI site 5' to the GUS gene at the start codon. Successful subcloning was confirmed by restriction analysis.

The Agrobacterium transformation plasmids were constructed by inserting the GUS expression cassettes as BstEII fragments into a descendent plasmid of pSB11 which contained the BAR expression cassette. Both the GUS, and BAR expression cassettes were located between the right and left T-DNA. The GUS cassette was inserted proximal to the right T-DNA border. The plasmid pSB11 was obtained from Japan Tobacco Inc. (Tokyo, Japan). The construction of pSB11 from pSB21 and the construction of pSB21 from starting vectors is described by Komari et al. (1996, Plant J. 10:165–174). The T-DNA of the plasmid was integrated into the superbinary plasmid pSB1 (Saito et al., EP 672 752 A1) by homologous recombination between the two plasmids. The plasmid pSB1 was also obtained from Japan Tobacco Inc.

Competent cells of the Agrobacterium strain LBA4404 harboring pSB1 were created using the protocol as described by Lin (1995) in Methods in Molecular Biology, ed. Nickoloff, J. A. (Humana Press, Totowa, N.J.) The plasmid containing the expression cassettes was electroporated into competent cells of the Agrobacterium strain LBA4404 harboring pSB1 to create the cointegrate plasmid in Agrobacterium using a BIO-RAD Micropulser (Cat# 165-2100, Hercules, Calif.). Electroporation was performed by mixing 1 ul of plasmid DNA (~100 ng) with 20 μl of competent Agrobacterium cells in a 0.2 cm electrode gap cuvette (Cat# 165-2086, BIO-RAD, Hercules, Calif.). Electroporation was performed using the EC2 setting, which delivers 2.5 kV to the cells. Successful recombination was verified by restriction analysis of the plasmid after transformation of the cointegrate plasmid back into *E. coli* DH5a cells.

Example 4

Transformation and Regeneration of Maize Callus via Agrobacterium

Preparation of Agrobacterium suspension:

Agrobacterium was streaked out from a −80° frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile ddH2O (stock solution A: K2HPO4 60.0 g/l, NaH2PO4 20.0 g/l, adjust pH to 7.0 w/KOH and autoclaved; stock solution B: NH4Cl 20.0 g/l, MgSO4.7H2O 6.0 g/l, KCl 3.0 g/l, CaCl2 0.20 g/l, FeSO4.7H2O 50.0 mg/l, autoclaved; stock solution C: glucose 5.56 g/l, agar 16.67 g/l (#A-7049, Sigma Chemicals, St. Louis, Mo.) and autoclaved).

The plate can be stored at 4° C. and used usually for about 1 month. A single colony was picked from the master plate and streaked onto a plate containing PHI-M medium [yeast extract (Difco) 5.0 g/l; peptone (Difco)10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU(N6) basal salts (Sigma C-1416) 4.0 g/l, Eriksson's vitamin mix (1000X, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2, 4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4'-hydroxyacetophenone, Aldrich chemicals) were added to a 14 ml Falcon tube in a hood. About 3 full loops (5 mm loop size) Agrobacterium was collected from the plate and suspended in the tube, then the tube vortexed to make an even suspension. One ml of the suspension was transferred to a spectrophotometer tube and the OD of the suspension adjusted to 0.72 at 550 nm by adding either more Agrobacterium or more of the same suspension medium, for an Agrobacterium concentration of approximately 0.5×109 cfu/ml to 1×109 cfu/ml. The final Agrobacterium suspension was aliquoted into 2 ml microcentrifuge tubes, each containing 1 ml of the suspension. The suspensions were then used as soon as possible.

Embryo Isolation, Infection and Co-cultivation:

About 2 ml of the same medium (here PHI-A or PHI-I) used for the Agrobacterium suspension were added into a 2 ml microcentrifuge tube. Immature embryos were isolated from a sterilized ear with a sterile spatula (Baxter Scientific Products S1565) and dropped directly into the medium in the tube. A total of about 100 embryos were placed in the tube. The optimal size of the embryos was about 1.0–1.2 mm. The cap was then closed on the tube and the tube vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of Agrobacterium suspension added to the embryos and the tube vortexed for 30 sec. The tube was allowed to stand for 5 min. in the hood. The suspension of Agrobacterium and embryos was poured into a Petri plate containing either PHI-B medium [CHU(N6) basal salts (Sigma C-1416) 4.0 g/l; Eriksson's vitamin mix (1000X, Sigma-1511) 1.0 ml/l; thiamine.HCl 0.5 mg/l; 2.4-D 1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine-.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube were transferred to the plate using a sterile spatula. The Agrobacterium suspension was drawn off and the embryos placed axis side down on the media. The plate was sealed with Parafilm tape or Pylon Vegetative Combine Tape (product named "E.G.CUT" and is available in 18 mm×50 m sections; Kyowa Ltd., Japan) and incubated in the dark at 23–25° C. for about 3 days of co-cultivation.

Resting, Selection and Regeneration Steps:

For the resting step, all of the embryos were transferred to a new plate containing PHI-C medium [CHU(N6) basal salts (Sigma C-1416) 4.0 g/l; Eriksson's vitamin mix (1000X Sigma-1511) 1.0 ml/l; thiamine.HCl 0.5 mg/l; 2.4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3–5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation.

For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000X, Sigma-1511) 1.0 ml/l; thiamine.HCl 0.5 mg/l; 2.4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time.; pH 5.8] putting about 20 embryos onto each plate.

The plates were sealed as described above and incubated in the dark at 28° C. for the first two weeks of selection. The embryos were transferred to fresh selection medium at two-week intervals. The tissue was subcultured by transferring to fresh selection medium for a total of about 2 months. The herbicide-resistant calli were then "bulked up" by growing on the same medium for another two weeks until the diameter of the calli was about 1.5–2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1–3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m-2sec-1) and 8 hrs. dark until shoots and roots developed. Each small plantlet was then transferred to a 25×150 mm tube containing PHI-F medium and grown under the same conditions for approximately another week. The plants were transplanted to pots with soil mixture in a greenhouse. GUS+ events are determined at the callus stage or regenerated plant stage. For Hi-II, an optimized protocol was: 0.5×109 cfu/ml Agrobacterium, a 3–5 day resting step, and no AgNO3 in the infection medium (PHI-A medium).

Example 5

Transformation of Maize by Particle Bombardment

The inventive polynucleotides contained within a vector are transformed into embryogenic maize callus by particle bombardment. Transgenic maize plants are produced by bombardment of embryogenically responsive immature embryos with tungsten particles associated with DNA plasmid. The plasmid contains a selectable and an unselectable marker gene.

Preparation of Particles

Fifteen mg of tungsten particles (General Electric), 0.5 to 1.8 μ, preferably 1 to 1.8μ, and most preferably 1μ, are added to 2 ml of concentrated nitric acid. This suspension is sonicated at 0° C. for 20 minutes (Branson Sonifier Model 450, 40% output, constant duty cycle). Tungsten particles are pelleted by centrifugation at 10000 rpm (Biofuge) for one minute, and the supernatant removed. Two milliliters of sterile distilled water are added to the pellet, and brief sonication used to resuspend the particles. The suspension is pelleted, one milliliter of absolute ethanol added to the pellet, and brief sonication used to resuspend the particles. Rinsing, pelleting, and resuspending of the particles is performed two more times with sterile distilled water, and finally the particles resuspended in two milliliters of sterile distilled water. The particles are subdivided into 250-ml aliquots and stored frozen.

Preparation of Particle-Plasmid DNA Association

The stock of tungsten particles is sonicated briefly in a water bath sonicator (Branson Sonifier Model 450, 20% output, constant duty cycle) and 50 ml transferred to a microfuge tube. Equimolar amounts of plasmid DNA are added to the particles for a final DNA amount of 0.1 to 10 mg in 10 ml total volume, and briefly sonicated: 1 mg total DNA is used. Fifty microliters of sterile aqueous 2.5 M CaCl2 are added, and the mixture briefly sonicated and vortexed. Twenty microliters of sterile aqueous 0.1 M spermidine are added and the mixture briefly sonicated and vortexed. The mixture is incubated at room temperature for 20 minutes with intermittent brief sonication. The particle suspension is centrifuged, and the supernatant removed. Two hundred fifty microliters of absolute ethanol are added to the pellet, followed by brief sonication. The suspension is pelleted, the supernatant removed, and 60 ml of absolute ethanol added. The suspension is sonicated briefly before loading the particle-DNA agglomeration onto macrocarriers.

Preparation of Tissue

Immature embryos of maize variety High Type II are the target for particle bombardment-mediated transformation. This genotype is the F1 of two purebred genetic lines, parents A and B, derived from the cross of two know maize inbreds, A188 and B73. Both parents are selected for high competence of somatic embryogenesis, according to Armstrong et al., Maize Genetics Coop. News 65:92 (1991).

Ears from F1 plants are selfed or sibbed, and embryos aseptically dissected from developing caryopses when the scutellum first became opaque. This stage occurs about 9–13 days post-pollination, and most generally about 10 days post-pollination, depending on growth conditions. The embryos are about 0.75 to 1.5 millimeters long. Ears are surface sterilized with 20–50% Clorox for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l AgNO3. Chu et al., Sci. Sin. 18:659 (1975); Eriksson, Physiol. Plant 18:976 (1965).

The medium is sterilized by autoclaving at 121° C. for 15 minutes and dispensed into 100×25 mm Petri dishes. AgNO3 is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole—the embryogenically responsive tissue—upwards from the culture medium. Ten embryos per dish are located in the center of a Petri dish in an area about 2 cm in diameter. The embryos are maintained on this medium for 3–16 hours, preferably 4 hours, in complete darkness at 28° C. just prior to bombardment with particles associated with plasmid DNA containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 ml are deposited on macrocarriers and the ethanol allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi are used. Multiple disks are used to effect a range of rupture pressures.

The shelf containing the plate with embryos is placed 5.1 cm below the bottom of the macrocarrier platform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 in Hg. After operation of the device, the vacuum is released and the Petri dish removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite, 0.85 mg/l Ag NO3 and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferate from the bombarded embryos. Putative transgenic tissue is rescued, and that tissue derived from individual embryos is considered to be an event and propagated independently on selection medium. Two cycles of clonal propagation are achieved by visual selection for the smallest contiguous fragments of organized embryogenic tissue.

For regeneration of transgenic plants, embryogenic tissue is subcultured to a medium comprising MS salts and vitamins (Murashige & Skoog, Physiol. Plant 15:473 (1962)), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm Petri dishes, and incubated in darkness at 28° C. until the development of well-formed, matured somatic embryos could be seen. This required about 14 days. Well-formed somatic embryos are opaque and cream-colored, and comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite in 100×25 mm Petri dishes and incubated under a 16 hour light::8 hour dark photoperiod and 40 meinsteinsm-2sec-1 from cool-white fluorescent tubes. After about 7 days, the somatic embryos germinate and produce a well-defined shoot and root. The individual plants are subcultured to germination medium in 125×25 mm glass tubes to allow further plant development. The plants are maintained under a 16 hour light:8 hour dark photoperiod and 40 meinsteinsm-2sec-1 from cool-white fluorescent tubes. After about 7 days, the plants are well-established and transplanted to horticultural soil, hardened off, and potted into commercial greenhouse soil mixture and grown to sexual maturity in a greenhouse.

Example 6

Expression Data Using Eap1 Regulatory Sequences

Immature seeds from 26 transgenic events were collected at specific intervals after pollination, starting at 2 days after pollination (DAP) and extending to physiological maturity. Each seed was dissected vertically from silk scar to pedicel and was examined by histochemical staining. Specifically, each section was incubated in a solution of 0.1 M sodium phosphate buffer, pH 7.0, containing 0.5% X-gluc (5-bromo-4-chloro-3-indolyl-β-D-glucuronic acid, sodium salt, dissolved in DMSO first) and 0.1% Triton X-100. Sections were incubated overnight at 37° C., but in some cases, sections were extensively stained within 2 to 3 hours.

The staining pattern showed the EAP1 promoter comes on at about 12DAP and lasts to at least 35DAP. It expresses primarily in the embryo with some aleurone expression.

In addition to harvesting developing seeds, silks, husks, leaves, tassels and roots were also collected. Variable expression was observed in leaves and roots of some events due to the presence of the 35S enhancer in the selectable marker.

All publications and patent applications mentioned in the specification are indicative of the level of those skilled in the art to which this invention pertains. All publications and patent applications are herein incorporated by reference to the same extent as if each individual publication or patent application is specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. An isolated promoter that regulates transcription in a seed embryo-preferred manner, wherein the promoter comprises the nucleotide sequences set forth in SEQ ID NO: 1.

2. An expression cassette comprising a promoter that regulates transcription in a seed embryo-preferred manner and a first nucleotide sequence operably linked to the promoter wherein the promoter comprises the nucleotide sequence set forth in SEQ ID NO: 1.

3. A plant stably transformed with an expression cassette comprising a promoter that regulates transcription in a seed embryo-preferred manner and a first nucleotide sequence operably linked to the promoter, wherein the promoter comprises the nucleotide sequence set forth in SEQ ID NO: 1.

4. The plant of claim 1, wherein the plant is a monocot.

5. The plant of claim 4, wherein the monocot is corn, wheat, rice, barley, sorghum, or rye.

6. A transgenic seed of the plant of claim 1.

7. A method for selectively expressing a nucleotide sequence in a plant seed, the method comprising transforming a plant cell with a transformation vector comprising an expression cassette, the expression cassette comprising a promoter that regulates transcription in a seed embryo-preferred manner and a first nucleotide sequence operably linked to the promoter, wherein the promoter comprises the nucleotide sequence set forth in SEQ ID NO: 1.

8. The method of claim 7 further comprising regenerating a stably transformed plant from the transformed plant cell; wherein expression of the first nucleotide sequences alters the phenotype of the plant seed.

9. The method of claim 7, wherein the plant cell is from a monocot.

10. The method of claim 7, wherein the plant is corn, wheat, rice, barley, sorghum, or rye.

* * * * *

UNITED STATES PATENT AND TRADEMARK OFFICE
CERTIFICATE OF CORRECTION

PATENT NO. : 7,081,566 B2  Page 1 of 1
APPLICATION NO. : 10/414588
DATED : June 25, 2006
INVENTOR(S) : Abbitt et al.

It is certified that error appears in the above-identified patent and that said Letters Patent is hereby corrected as shown below:

Column 29,
Line 33 should read as follows:
-- The plant of claim 3, wherein the plant is a monocot. --

Column 29,
Line 36 should read as follows:
-- A transgenic seed of the plant of claim 3. --

Signed and Sealed this

Twenty-first Day of November, 2006

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 1268
<212> TYPE: DNA
<213> ORGANISM: Zea mays
<220> FEATURE:
<221> NAME/KEY: promoter
<222> LOCATION: (1)...(1268)

<400> SEQUENCE: 1
gcagcggggc cgatgaagtc gaagcagcag ggtcgacgac aagatcgcga gcagtcgcgt        60
gatgacgctt actaaaaacc ttattcgccc tctcccgatg caagatctcg aatgcgaagg       120
gttccggaga cctgctctcc tgaacgcaga tgcacgtcgg cgattgggat ggcggcgcag       180
ttgtgagcag agggccttat ataggccgt gtccgcgaac cgataacgat ccgcgatccg       240
atctacatgt tatctacgaa tcgatagact cgcgttccgt tcagatcctt atcgcgatcg       300
```

-continued

```
gttagggctc taacttaaca gccaagcaac cgccctggcc cggcgaggcg agcgcgtgtg      360
gttctccaca ctctctcctc tcatccatga cttgttgagt gagtgtagca tccatattta      420
aactagttcc actccacttg gactagcaat atggcactat atgttccacc attccctagc      480
cataccatac atgggttttt gagatttttt tagaatttaa ttaaatttct caattgagtc      540
tagcccataa atccaacacg atataagtct atctgtcgct ggtagattga gagaggatgt      600
gtgcatgtct gtaaataaaa aaagttgtt tttacacata aattgcgcta tgactttaca       660
tgaaataaat tttctaaaat ttaaaactta cataagtaaa aaaaaatata agaaggaaa       720 gaaacacgac atggaaaaaa tctctcgttg ttttatatgg atgcaacagc tgcagtcccc      780
gtgcaagcga tgctcatccg ttcccatggc gtgcacggcc cagaaacgac acgcttcacc      840
tactttcttc cctgccacca cacccaccgt ccacccacac cacaccgcgc gccacgcgcc      900
cacggcacct cggctcagtg tcgtcgcatg tcgctcacgt actgtcgcag aactcacacc      960
gtcacacggt gcctgctatc tagctaatgc tgctagcagc catgtcacac cgatataacc     1020
cggccaccgc gcgccgcgcc acgtcgccat gcacgcggcc acgtccccca tcgatcgacg     1080
tcgtcctcct catcctggct cctccggatc catccccgcg ctcctataaa tacctcgtct     1140
catgctcggc catgtacatc gacccagcca tctcctcacc ctcgttcacc acacagtccg     1200
ccactccttt agtagcttgt gatttgtacg tcgacgagat cactggtcgg gtgagcgctc     1260
gacgactc                                                              1268
```

<210> SEQ ID NO 2
<211> LENGTH: 762
<212> TYPE: DNA
<213> ORGANISM: Zea mays
<220> FEATURE:
<221> NAME/KEY: terminator
<222> LOCATION: (1)...(762)

<400> SEQUENCE: 2

```
taataaaagg gtagtgtacg cttaccgcgt acgtacgtgt caccgggcgt ggcactctcc       60
agtctccagg gacccatcca ccaaatgcta ctgctccttc gtagggagac gtgggaataa     120
agagtggtag ctgcatgcac gtacggcggc catggctctc cgatgagaga gctagctgtg    180
tacgtgtgtt cttgatgttg ttccatgcat gacatgtata cgtcttgcct aagtacgctt    240
gtactagttg agagactgtg taagtgaaat gtgctataat aataaataag taaaaggcgc    300
cttctccaac attctatggg ctcgtttggg agggttgcgg ctcctctcaa aacggctcca    360
gctccaactc ctccaaagag tagctcctct gaggagccat gcttttgca atcgtttgct     420 aaaaaacggc tccttgtgta tgccgtgctc atcatcatca acgttgatta cctagaaatc    480
actgcagtgc tttctgttgt cggatagtgg aaggctcctt gtgtattatt acaacaaaaa    540
aatattatgg agtaatatta gaaaagcatt tgcacatcca aatccataca caagtcatat    600
atcacttgga tgattaccta gaaagaaaga tcgctcttgc gcgatgtcat cacgaaacct    660
atccatcata cgatcattag agtatggaca tgatgagtca gttgtatttc tatatctaaa    720
aggtatagtg ggcacgtaat ctggatttcg atcgcactta ta                       762
```

<210> SEQ ID NO 3
<211> LENGTH: 37
<212> TYPE: DNA
<213> ORGANISM: Artificial Sequence
<220> FEATURE:
<223> OTHER INFORMATION: Promoter primer 1

-continued

```
<400> SEQUENCE: 3
aagcttgata tcgcagcggg gccgatgaag tcgaagc                                37

<210> SEQ ID NO 4
<211> LENGTH: 44
<212> TYPE: DNA
<213> ORGANISM: Artificial Sequence
<220> FEATURE:
<223> OTHER INFORMATION: Promoter primer 2

<400> SEQUENCE: 4
tcatgagtcg tcgagcgctc acccgaccag tgatctcgtc gacg                        44

<210> SEQ ID NO 5
<211> LENGTH: 50
<212> TYPE: DNA
<213> ORGANISM: Artificial Sequence
<220> FEATURE:
<223> OTHER INFORMATION: Terminator primer 1

<400> SEQUENCE: 5
tcatgaagat ctgtcgactc tagacccggg taataaaagg gtagtgtacg                  50

<210> SEQ ID NO 6
<211> LENGTH: 26
<212> TYPE: DNA
<213> ORGANISM: Artificial Sequence
<220> FEATURE:
<223> OTHER INFORMATION: Terminator primer 2

<400> SEQUENCE: 6
gggccctata agtgcgatcg aaatcc                                            26

<210> SEQ ID NO 7
<211> LENGTH: 1092
<212> TYPE: DNA
<213> ORGANISM: Zea mays
<220> FEATURE:
<221> NAME/KEY: CDS
<222> LOCATION: (1)...(1092)
<220> FEATURE:
<221> NAME/KEY: misc_feature
<222> LOCATION: 940
<223> OTHER INFORMATION: n = A,T,C or G

<400> SEQUENCE: 7 atg ggg aag ggt agt gtg ggt gca tca tgg tgg gcg ttc ctc ctg ctc        48
Met Gly Lys Gly Ser Val Gly Ala Ser Trp Trp Ala Phe Leu Leu Leu
 1               5                   10                  15 gcc ggc gtg ctg ctg gtc gta gca gcc acg gcc ggg gcg gag gac gga        96
Ala Gly Val Leu Leu Val Val Ala Ala Thr Ala Gly Ala Glu Asp Gly
             20                  25                  30 gtg gtc gaa cgg gac cgc aag gag gac ctg cgg tgg tgc aag cag gcg       144
Val Val Glu Arg Asp Arg Lys Glu Asp Leu Arg Trp Cys Lys Gln Ala
         35                  40                  45 tgc gag tgg cag tac gga aag gac acc ccg cgg aag agg gaa tgc gag       192
Cys Glu Trp Gln Tyr Gly Lys Asp Thr Pro Arg Lys Arg Glu Cys Glu
     50                  55                  60 agc gag tgc cgc gag cgg cac cag caa gct gac gcg ggc gag gac ggc       240
Ser Glu Cys Arg Glu Arg His Gln Gln Ala Asp Ala Gly Glu Asp Gly
 65                  70                  75                  80 gac agc ggc gtg gac gcc tac gtc tcc cgc tcc ggg agg ggc gag tgc       288
Asp Ser Gly Val Asp Ala Tyr Val Ser Arg Ser Gly Arg Gly Glu Cys
                 85                  90                  95
```

```
cgg cgc cag tgc ctg cgc cgc cac gag ggc cag ccg tgg gag acc cag    336
Arg Arg Gln Cys Leu Arg Arg His Glu Gly Gln Pro Trp Glu Thr Gln
        100                 105                 110 gag tgc atg agg cgg tgc cgc cgc cgc gga ctg gcc gtc gac atg gag    384
Glu Cys Met Arg Arg Cys Arg Arg Arg Gly Leu Ala Val Asp Met Glu
            115                 120                 125 caa gag tac ggt cgc ggc agc gag agc gcg ggc aag tgc cgg gag agg    432
Gln Glu Tyr Gly Arg Gly Ser Glu Ser Ala Gly Lys Cys Arg Glu Arg
    130                 135                 140 tgc gag cgc cac cac cgc ggg gac tgg tgg gag agg cag cgc tgc ctg    480
Cys Glu Arg His His Arg Gly Asp Trp Trp Glu Arg Gln Arg Cys Leu
145                 150                 155                 160 atg gac tgc aag agc cgg gag cgg gag gag ggc ggc agc ggc gag gag    528
Met Asp Cys Lys Ser Arg Glu Arg Glu Glu Gly Gly Ser Gly Glu Glu
                165                 170                 175 gag gag gag gac agc ggc gac cgc tgc cct tgc gag aag cag tgc gag    576
Glu Glu Glu Asp Ser Gly Asp Arg Cys Pro Cys Glu Lys Gln Cys Glu
            180                 185                 190 ggc cac cac gac cgg gaa agc agg cag cag tgc gtc cag gct tgc gag    624
Gly His His Asp Arg Glu Ser Arg Gln Gln Cys Val Gln Ala Cys Glu
    195                 200                 205 cgc cgg cga cag gag cgc ggc ggc agc cgt gac tcc gac gtc gac gag    672
Arg Arg Arg Gln Glu Arg Gly Gly Ser Arg Asp Ser Asp Val Asp Glu
210                 215                 220 gac gac agc gac cgg cgg tgc cag atg aaa tgc cgg cgc cac agc gat    720
Asp Asp Ser Asp Arg Arg Cys Gln Met Lys Cys Arg Arg His Ser Asp
225                 230                 235                 240 cgg cag gcg agg cag tgg tgc gtg cag cgc tgc gag cgt aag caa cag    768
Arg Gln Ala Arg Gln Trp Cys Val Gln Arg Cys Glu Arg Lys Gln Gln
                245                 250                 255 gag gac gcc gcc gcc gac gac gac gag aac agc gac cgg tgc cag aag    816
Glu Asp Ala Ala Ala Asp Asp Asp Glu Asn Ser Asp Arg Cys Gln Lys
            260                 265                 270 aga tgc cag cac cac agc gac tgg atg aaa agg ctg cgg tgc atg caa    864
Arg Cys Gln His His Ser Asp Trp Met Lys Arg Leu Arg Cys Met Gln
    275                 280                 285 cgg tgc ggg cga cag gag gag ggc ggc gca cgc gac gac gct gac gac    912
Arg Cys Gly Arg Gln Glu Glu Gly Gly Ala Arg Asp Asp Ala Asp Asp
290                 295                 300 gag gcc agc cac ggc gac cgg tgc cgg nga aga agt gcc agc agc acc    960
Glu Ala Ser His Gly Asp Arg Cys Arg Xaa Arg Ser Ala Ser Ser Thr
305                 310                 315                 320 acc gcg act acg aca aga agc agc agt gcg tgc gcg act gcc gcc gcg   1008
Thr Ala Thr Thr Thr Arg Ser Ser Ser Ala Cys Ala Thr Ala Ala Ala
                325                 330                 335 gcc gtg gct ggg aaa cgg tgg ccg gcg cca tcc ttg agg tgg tgt gac   1056
Ala Val Ala Gly Lys Arg Trp Pro Ala Pro Ser Leu Arg Trp Cys Asp
            340                 345                 350 gat cga cga cgt gca tgg cgt ggc gca cag agc tag               1092
Asp Arg Arg Arg Ala Trp Arg Gly Ala Gln Ser *
    355                 360
```

<210> SEQ ID NO 8  
<211> LENGTH: 363  
<212> TYPE: PRT  
<213> ORGANISM: Zea mays  
<220> FEATURE:  
<221> NAME/KEY: VARIANT  
<222> LOCATION: 314  
<223> OTHER INFORMATION: Xaa = Any Amino Acid

<400> SEQUENCE: 8

| | | | | | | | | | | | | | | |
|---|---|---|---|---|---|---|---|---|---|---|---|---|---|---|
|Met|Gly|Lys|Gly|Ser|Val|Gly|Ala|Ser|Trp|Trp|Ala|Phe|Leu|Leu|Leu|
|1| | | |5| | | | |10| | | | |15| |

Ala Gly Val Leu Leu Val Val Ala Ala Thr Ala Gly Ala Glu Asp Gly
        20              25              30

Val Val Glu Arg Asp Arg Lys Glu Asp Leu Arg Trp Cys Lys Gln Ala
        35              40              45

Cys Glu Trp Gln Tyr Gly Lys Asp Thr Pro Arg Lys Arg Glu Cys Glu
    50              55              60

Ser Glu Cys Arg Glu Arg His Gln Gln Ala Asp Ala Gly Glu Asp Gly
65              70              75              80

Asp Ser Gly Val Asp Ala Tyr Val Ser Arg Ser Gly Arg Gly Glu Cys
            85              90              95

Arg Arg Gln Cys Leu Arg Arg His Glu Gly Gln Pro Trp Glu Thr Gln
        100             105            110

Glu Cys Met Arg Cys Arg Arg Gly Leu Ala Val Asp Met Glu
        115             120            125

Gln Glu Tyr Gly Arg Gly Ser Glu Ser Ala Gly Lys Cys Arg Glu Arg
130              135              140

Cys Glu Arg His His Arg Gly Asp Trp Trp Glu Arg Gln Arg Cys Leu
145              150            155              160

Met Asp Cys Lys Ser Arg Glu Arg Glu Glu Gly Ser Gly Glu Glu
        165             170            175

Glu Glu Glu Asp Ser Gly Asp Arg Cys Pro Cys Glu Lys Gln Cys Glu
        180             185            190

Gly His His Asp Arg Glu Ser Arg Gln Gln Cys Val Gln Ala Cys Glu
        195             200            205

Arg Arg Arg Gln Glu Arg Gly Gly Ser Arg Asp Ser Asp Val Asp Glu
210              215            220

Asp Asp Ser Asp Arg Arg Cys Gln Met Lys Cys Arg Arg His Ser Asp
225              230            235            240

Arg Gln Ala Arg Gln Trp Cys Val Gln Arg Cys Glu Arg Lys Gln Gln
        245             250            255

Glu Asp Ala Ala Ala Asp Asp Glu Asn Ser Asp Arg Cys Gln Lys
        260             265            270

Arg Cys Gln His His Ser Asp Trp Met Lys Arg Leu Arg Cys Met Gln
        275             280            285

Arg Cys Gly Arg Gln Glu Glu Gly Gly Ala Arg Asp Asp Ala Asp Asp
        290             295            300

Glu Ala Ser His Gly Asp Arg Cys Arg Xaa Arg Ser Ala Ser Ser Thr
305              310            315            320

Thr Ala Thr Thr Thr Arg Ser Ser Ala Cys Ala Thr Ala Ala Ala
              325            330            335

Ala Val Ala Gly Lys Arg Trp Pro Ala Pro Ser Leu Arg Trp Cys Asp
        340             345            350

Asp Arg Arg Ala Trp Arg Gly Ala Gln Ser
        355             360

<210> SEQ ID NO 9
<211> LENGTH: 22
<212> TYPE: DNA
<213> ORGANISM: Artificial Sequence
<220> FEATURE:
<223> OTHER INFORMATION: PCR primer

```
<400> SEQUENCE: 9
ccatggggaa gggtagtgtg gg                                          22

<210> SEQ ID NO 10
<211> LENGTH: 26
<212> TYPE: DNA
<213> ORGANISM: Artificial Sequence
<220> FEATURE:
<223> OTHER INFORMATION: PCR primer

<400> SEQUENCE: 10
cccgggtcac accacctcaa ggatgg                                      26
```